United States Patent
Dreger et al.

(10) Patent No.: US 9,550,978 B2
(45) Date of Patent: Jan. 24, 2017

(54) ISOLATION AND FUNCTIONAL IDENTIFICATION OF CELLS

(75) Inventors: Mathias Dreger, Berlin (DE); Thomas Lenz, Berlin (DE); Christian Dalhoff, Berlin (DE); Michael Joachim Sefkow, Berlin (DE)

(73) Assignee: CAPROTEC BIOANALYTICS GMBH (DE)

( * ) Notice: Subject to any disclaimer, the term of this patent is extended or adjusted under 35 U.S.C. 154(b) by 604 days.

(21) Appl. No.: 13/884,614

(22) PCT Filed: Nov. 11, 2011

(86) PCT No.: PCT/EP2011/069959
§ 371 (c)(1),
(2), (4) Date: Jul. 18, 2013

(87) PCT Pub. No.: WO2012/062910
PCT Pub. Date: May 18, 2012

(65) Prior Publication Data
US 2013/0295636 A1    Nov. 7, 2013

(30) Foreign Application Priority Data
Nov. 11, 2010  (DE) .................. 10 2010 060 498

(51) Int. Cl.
*C12N 5/09* (2010.01)
*G01N 33/50* (2006.01)
*G01N 33/58* (2006.01)

(52) U.S. Cl.
CPC ......... *C12N 5/0693* (2013.01); *G01N 33/5005* (2013.01); *G01N 33/585* (2013.01)

(58) Field of Classification Search
CPC .. G01N 33/5005; G01N 33/585; C12N 5/0693
See application file for complete search history.

(56) References Cited

U.S. PATENT DOCUMENTS

| 5,541,072 A * | 7/1996 | Wang ........................ B03C 1/01 209/214 |
| 8,268,264 B2 * | 9/2012 | Lenz ..................... B03C 1/0332 422/500 |
| 2003/0119021 A1 * | 6/2003 | Koster ................. C12Q 1/6834 435/6.12 |
| 2012/0230994 A1 * | 9/2012 | Pan .................. A61K 47/48346 424/134.1 |

FOREIGN PATENT DOCUMENTS

WO   WO 2009/142525   11/2009

OTHER PUBLICATIONS

Fischer et al: "Capture compound mass spectrometry sheds light on the molecular mechanisms of liver toxicity of two Parkinson drugs", Toxicological Sciences, vol. 113, Jan. 1, 2010, pp. 243-253.
Luo et al: "The cAMP capture compound mass spectrometry as a novel tool for targeting cAMP-binding proteins: from protein kinase A to potassium/sodium hyperpolarization-activated cyclic nucleotide-gated channels", Moldecular and Cellular Proteomics, vol. 8, Dec. 1, 2009, pp. 2843-2856.

* cited by examiner

*Primary Examiner* — Shafiqul Haq
(74) *Attorney, Agent, or Firm* — JMB Davis Ben-David (57) ABSTRACT

The invention relates to a method for tagging, identifying and isolating a target cell, wherein the cell is contacted with a capture compound comprising a small molecule moiety, for example a pharmaceutical drug molecule, capable of selectively binding with the cell surface of the target cell, and a function that is capable to covalently or quasi-covalently bind to a surface as a marker or tagging function. In some embodiments the capture compound also includes a photoactivatable reactivity function. The capture compound attaches to a particle that mediates identification or isolation of the tagged cell.

14 Claims, 4 Drawing Sheets

ISOLATION AND FUNCTIONAL IDENTIFICATION OF CELLS

The present invention relates to a method for tagging and isolating cells, particularly for diagnosis and therapy of diseases. Tagging and isolation is achieved by attaching the target cell to a particle or surface and removing, where isolation is the objective, the cell from its environment.

Identifying and isolating functionally or phenotypically defined cell populations is an important challenge in basic research, but also with view to the development of novel methods for diagnosing and treating disease. One field in which identification and isolation of cells is important is oncology, where early identification of circulating tumour cells, indicating a relapse in a patient, may enable earlier treatment. Known methods for detection of circulating tumour cells make use of antibodies raised against tumour-specific surface structures binding non-covalently to tumour cells. Such methods are restricted by the availability, specificity and affinity of suitable antibodies.

In some cases, tumour-specific cell surface structures are formed by the interaction of several distinct proteins. In such cases, addressing of the target by antibodies specific for the single protein components of the target structure would not work, since the individual components have a far less specific distribution on different cell types.

Matrix metalloproteinases (MMP) play an important roll in assembly and decomposition of tissues, cell migration and adhesion. Their expression correlates with malignity in different tumor entities. Different ligands for MMP are known. Marimastat, a succinylhydroxamate, was tested in the clinic. The mechanism of action of succinylhydroxamate inhibitors is postulated to be the complexation by the hydroxamate moiety of the zinc ion in the active center of MMP.

Trifunctional capture compounds comprising a drug derivate as selectivity function, a photoactivatable moiety as reactivity function and a sorting function are know from WO2004/064972A2. This document also shows the application of Trifunctional capture compounds to in-vitro analysis of protein homogenates in the context of proteomics research.

The objective of the present invention is to provide means and methods for recognizing, marking or tagging cells, particularly tumor cells with metastatic potential, with high sensitivity and selectivity, and to enable the isolation of such cells. This objective is obtained by the subject matter of the independent claims.

In the context, the following terms are being used in the sense detailed below:

A target cell in the context of the present invention is a eukaryotic or prokaryotic cell characterized by functional, phenotypical or genotypical features. The target cell is to be tagged, identified or isolated according to the invention, by means of interaction of small molecules with structures present on the surface of the target cell. A target cell has an essentially intact structure and—as far as the target cell is not part of a histological sample—an intact metabolism. A target cell is—to the degree typical for the particular cell type chosen—able to divide, at least prior to being tagged or isolated by the method of the invention.

A photo-activatable function is a moiety that can be induced to form a reactive species, for example a nitrene or carbene or a radical, by electromagnetic radiation, e.g. visible light. The reactive species can then rapidly engage to form a covalent bond with a suitable partner, for example by addition to a C=C double bond or by insertion into an XH bond (where X is sulphur, oxygen, nitrogen or carbon).

A cell surface target structure is a protein specifically expressed on the surface of a target cell, or a plurality of proteins specifically expressed on the surface of a target cell forming a protein complex the existence of which is specific for the target cell.

A small molecule moiety in the context of the present invention is a compound of less than 3500 u molecular mass able to specifically and selectively interact with a cell surface target structure. For all aspects and embodiments of the present invention, short peptides and pharmaceutical drug-like "small molecule" drugs of below 1000 u molecular mass, below 800 u, below 700 u, below 500 u or less down to 160 u (the "Lipinski" lower limit of molecular mass) are preferred modalities of practicing the invention. A small molecule moiety in the context discussed herein is synonymous to "selectivity function" and is generally attached to a capture compound or a second surface entity. Biotin is excluded from the definition of small molecule moiety. A small molecule moiety in the sense used herein is one for which binding sites exist.

The general principle underlying the invention is the surprising finding that cells may be tagged with particles, or attached to solid surfaces, by making use of the interaction of cell surface target structures such as membrane-bound proteins with particle-bound small molecule moiety ligands to these proteins. Such ligands may be small molecule drugs. Surprisingly the interaction or binding of the particles, mediated by only the binding of a drug to its binding site, or by a short peptide to its respective recognition site, is sufficiently strong to withstand washing steps for removing unattached particles, and even strong enough to retain the cells in a magnetic field for separation from magnetic-particle-tagged cells from untagged cells.

Furthermore, the protein-ligand interaction may be combined, according to some aspects and embodiments of the present invention, with a light-induced covalent bond brought about by activating a "reactivity" function in spatial proximity to the small molecule moiety. Covalently binding the particle to the cell surface strengthens the particle's attachment to the cell and broadens the range of applicable methodologies for tagging and isolating cells.

According to a first aspect of the invention, a method for tagging or marking a target cell comprises contacting the cell surface of the target cell with a second surface of, for example, a particle or a vial, whereby the target cell attaches to said second surface.

As a first alternative embodiment of this aspect of the invention, the second surface comprises a capture compound attached covalently or quasi-covalently on the second surface. Said capture compound comprises a small molecule moiety of below 3500 u, <3000 u, <2500 u, <2000 u, <1500 u, <1000 u, <800 u or <500 u molecular mass ("selectivity function") capable of selectively binding to a target cell surface feature on said cell surface, for example a cell surface protein or a complex of cell surface proteins. Attachment of the small molecule moiety is achieved by non-covalent interaction and is characterized by high selectivity and affinity, the dissociation constant being typically below 100 µmol/l, <10 µmol/l, <1 µmol/l, <100 nmol/l, <10 nmol/l or even <1 nmol/l. A typical example for such interactions of a small molecule moiety to a cell surface structure is the interaction of a small molecule pharmaceutical drug or a peptide hormone with the respective molecule's interaction partner, a cell surface target protein or target protein complex on the surface of the target cell.

As a second alternative embodiment, the attachment of the second surface to the cell surface is mediated by first attaching a capture compound to the target cell surface. In this embodiment, the target cell is contacted with a capture compound which comprises a small molecule moiety of below 3500 u molecular mass capable of selectively binding to said cell surface, as set forth above. Reversible attachment of the small molecule moiety is achieved by non-covalent interaction and is characterized by high selectivity and affinity. Small molecule pharmaceutical drug moieties or peptide hormones are non-limiting examples. Said capture compound further comprises a sorting function, by which the capture compound can selectively be attached to said second surface. Excess capture compound may be removed, e.g. by washing, and in a second step, a second surface capable of binding selectively to the sorting function is contacted with the cell. Such sorting function may be, by way of non-limiting example, a biotin moiety that binds to streptavidin present on the second surface. Likewise, the sorting function may be an oligonucleotide strand attaching to a complementary strand attached to said second surface, or a disulphide bridge-containing linker attaching to a gold (second) surface.

Thus, the capture compound is attached to a second surface (i.e. a surface different from the surface of the target cell) either a) before attaching the capture compound to the target cell selectively by means of interaction of the small molecule moiety with a protein or protein complex on the surface of the target cell, or b) after attaching the capture compound, by linking the capture compound through a sorting function to a solid or particulate second surface. Alternative a) depends on the second surface having reacted with or attached to the capture compound first, and letting the target cell interact by means of the selectivity function (small molecule moiety) to the second surface subsequently. According to alternative b) the capture compound is first linked to the target cell and then sorted to the second surface.

According to another aspect of the invention, a method for isolating a target cell from an environment such as a cell suspension, blood or biopsy sample comprises tagging method laid out above, and subsequently removes the second surface from the environment, or removes the environment from the surface. This separation is relative and depends on perspective; in embodiments for which the surface is that of a particle, the cell with attached particle will be deemed removed from its environment; in embodiments in which the surface is the stationary phase of a cartridge and a blood sample is pumped across a fibre filling, the separation will be regarded as one of environment from sample. The effect is the same.

According to one embodiment, the second surface or the capture compound further comprises a reactivity function that can be activated by light (photo-activatable), in addition to the selectivity function (and the sorting functions in embodiments that make use of a capture compound). The small molecule moiety thus mediates selective non-covalent attachment of the surface or capture compound to the target cell surface based on the affinity of the small molecule moiety to a binding site present on the cell surface. Subsequent to this attachment, a covalent bond is made non-specifically at a site close to the binding site of the small molecule moiety. This covalent bond to the cell surface is generated by light (electromagnetic radiation) activation of the reactivity function.

The photo-activatable reactivity function, according to any applicable aspect or embodiment of the invention that features this function, is a group that is activated by light (visible, UV, IR or electromagnetic radiation of higher energy) to form a highly reactive intermediate. Non-limiting examples are moieties that upon activation by light generate a carbene by photolysis of a diazo compound, such as a diazirine, or generate a nitrene from an azide, or that generate a radical from a carbon-hetero-compound as is the case in photolysis of a benzophenone. The formed highly active intermediate then reacts with any proximate group such as an aromatic amino acid side chain, an alcohol, thiole or amine function.

Non-limiting examples for reactivity functions are aryl-trifluoromethyldiazirine (II), arylazide (III) or benzophenone (IV):

Non-limiting examples for the second surface are the surface of a particle, a chromatographic stationary phase, a solid surface of a chip or microtitre plate, or a fibre.

In one embodiment, the (second) surface, which contacts the cell surface according to the first aspect of the invention and mediates separation according to the second aspect of the invention, is the surface of a particle, attachment of which to the cell surface tags or marks the target cell. The tagged or marked cell may be identified by light microscopy or other optical methods (as one non-limiting example, light scattering as can be measured in a fluorescence activated cell sorting (FACS) machine). An optional washing step may precede the visualization.

In one embodiment, the particle is a gold particle of approximately 5 nm, 10 nm, 20 nm, 30 nm, 50 nm, 75 nm, 100 nm or 150 nm diameter.

In one embodiment, the particle is a magnetic particle, preferably a superparamagnetic particle, of 10 nm, 25 nm, 50 nm, 100 nm, 250 nm, 500 nm, 1 μm, 3 μm, 5 μm, 10 μm or 20 μm diameter.

The previously described embodiments offer advantages because of their simplicity, as the attachment of a particle (or the attachment of a cell to a solid surface, as the case may be) can be visualized by light microscopy, compared to methods known in the art that employ antibody-linked dyes for marking, and fluorescence microscopy for detection. The latter requires costly reagents and apparatus.

According to one embodiment, the reactivity function and the small molecule moiety selectivity function are linked by a central capture compound core moiety Z. Therein, the binding of the small molecule moiety and the reactivity function are mediated by a capture compound that comprises an at least tri-functional central core Z, to which the small molecule moiety, the reactivity function and the sorting or tagging function for binding to the surface are each individually attached covalently.

Z is a central element consisting of, in the extreme, 1 atom such as carbon or nitrogen, or a short chain of <10 atoms of molecular mass 12 or higher. Non-limiting examples for Z are amino acids having OH—, SH—, $NH_2$—, $CONH_2$, COOH—, or —$NHNH_2$—$NH_2$ moieties in their side chain (such as serine, threonine, cysteine, lysine, glutamin acid, glutamine or arginine), since they can be derivatised in three different positions independently without much synthetic effort.

For embodiments making use of a three-functional capture compound, the small molecule moiety, reactivity function and sorting function are each individually attached to a central core moiety Z by means of short linkers (carbon or heteroatom-carbon chains of one to about twenty atoms chain length), or directly. Individual attachment to a central core implies that these functions can rotate in space individually, distorting if at all, only minimally the binding of the small molecule moiety (selectivity function) to its target. Furthermore, if one or two sufficiently long spacers are chosen between the selectivity and reactivity function and Z, respectively, the covalent attachment may be effected to a cell surface protein different from the one to which the selectivity function binds, thereby adding a layer of information about protein expression of the target cells that may be accessed if the target cell is later isolated.

According to another aspect of the invention, a surface for tagging or isolating a target cell comprises a small molecule moiety capable of selectively interacting with the surface of the target cell, and an activatable reactivity function. According to one embodiment, the surface is a particle surface. Thereby, a particle is provided for marking or tagging target cells, wherein the particle comprises a small molecule moiety capable of selectively interacting with and attaching to proteins or protein complexes on the target cell surface, and a photoactivatable reactivity function. Optionally, the small molecule (selectivity) moiety and the reactivity function are linked by an at least trifunctional moiety Z to which the small molecule moiety, the reactivity function and the particle are each attached.

According to one embodiment, the surface is the surface of a magnetic particle, for example a superparamagnetic particle, of 10 nm, 25 nm, 50 nm, 100 nm, 250 nm, 500 nm, 1 μm, 3 μm, 5 μm, 10 μm or 20 μm diameter. In one embodiment, the surface is that of a gold particle of approximately 5 nm, 10 nm, 20 nm, 30 nm, 50 nm, 75 nm, 100 nm or 150 nm diameter. In one embodiment, the surface is covered by biocompatible material such as, by way of non-limiting example, sugar moieties. In one embodiment, the second surface has capture compounds attached to it comprising small molecule moieties and photoactivatable moieties linked through a short bridge or a central core Z, and the capture compound is attached to the second surface by a biotin-streptavidin bond. In one embodiment, the small molecule moiety is attached directly on the surface of the particle by suitable linkers, for example polyethyleneoxide spacers or one or more lysines, and the reactivity function is attached to the second surface separately though the same or different linker chemistry.

Thus, attachment of the target cell can be achieved by having the small molecule moiety and the reactivity function bind separately to the second surface, each having its own linker, or both small molecule moiety and reactivity function can be present in one molecule, which itself is attached to the second surface.

According to one embodiment, the surface is a fibre (or hollow fibre for enhancing the surface area) or a coarse grained material. This embodiment allows providing the second surface material in a cartridge or other flow-through compartment, into which a suspension containing target cells can be directed. Attachment of the target cells contained in the suspension depletes these target cells therein, allowing the depletion of particular target cells such as tumour cells from blood or other fluids.

The attachment of the cell to the small molecule moiety is reversible at first, allowing the cell to release from the second surface in the flow if the equilibrium of the small molecule moiety with its target structure allow for disengagement. By photoactivation of the reactivity function—where provided depending on the embodiment—an irreversible covalent bond is made between the target cell surface and the second surface. After the activation of the reactivity function and subsequent covalent linking, the target cell cannot be dissociated from the second surface without rupturing the link between the target cell surface structure to which the covalent link exists, and the cell membrane. Activation can proceed continuously or pulsed.

Cells attached to the second surface through interaction with the small molecule moiety (selectivity function) are retained selectively. Dependent on reaction conditions and the parameters of flow, a certain degree of non-target cells may be retained also. In some embodiments, such binding of non-target cells may be acceptable, as a decrease in selectivity can be the price to pay for an optimal depletion or removal of target cells from the suspension. In order to remove target cells as completely as possible from an environment such as a blood sample, one embodiment provides for a circular flow of the sample over the second surface several times.

According to one embodiment of any aspect of the invention shown herein, the second surface is the surface of a gold particle. Gold particles are particularly amenable to linking of organic compounds to their surface by sulphur (SH, R—S—S—R) bridges. A capture compound linked to gold particles is therefore obtainable cheaply and allows for an economic use, for example in serial examination of histological samples.

According to one embodiment of any aspect of the invention shown herein, the second surface is the surface of a magnetic particle. Magnetic particles are easily removed from an environment, with the target cells attached. Preferred magnetic particles are superparamagnetic, i.e. they do not show permanent magnetisation upon removal of the magnetic field, making them particularly amenable to suspenions.

According to another embodiment, a particle is provided that has a diameter of 5 nm, 10 nm, 25 nm, 50 nm, 100 nm, 250 nm, 500 nm, 1 μm, 3 μm, 5 μm, 10 μm or 20 μm and an MMP inhibitor of the hydroxamate class, for example marimastat. In preferred alternatives of this embodiment, the particle is a superparamagnetic particle or a gold particle.

The small molecule moiety or selectivity function referred to in any aspect or embodiment of the invention can be a short peptide, according to any previously mentioned aspect or embodiment of the invention. According to one embodiment, it has a molecular mass of about 3500 u to about 900 u, as it is typical for cell surface binding peptides such as CGRP (calcitonin gene related peptide; Uniprot ID P10092), bradykinin (CAS No. 58-82-2; Uniprot ID P01042) or substance P (CAS 33507-63-0; Uniprot ID P20366). Similarly, the selectivity function can be a small molecule, preferably one conforming to the "Lipinski rules", i.e. the molecule moiety has a molecular mass between 160 u and 500 u, up to five hydrogen bond donors (oxygen or nitrogen atoms with bound hydrogen) and up to ten hydrogen bond acceptors (oxygen or nitrogen) and an octanol-water partition coefficient log P of below 5.6 (calculated for the free small molecule forming the moiety). According to one embodiment the selectivity function is a small molecule moiety of below 1000 u or below 700 u molecular mass, or even below 500 u. The atoms forming the part of the capture compound that is not the small molecule moiety shall not count toward the 500 u or 3500 u molecular mass limit. Preferred embodiments are those for which the selectivity function is a pharmaceutical drug or a drug development candidate.

According to one preferred embodiment of any aspect of the invention, the small molecule moiety is a ligand molecule for matrix metalloproteinases (MMP). Capture compounds comprising a small molecule moiety having a dissociation constant of <1 μmol/l for a cell surface MMP protein or MMP protein complex are preferred. Also preferred are capture compounds comprising a hydroxamate moiety. Examples of small molecule moieties in particularly preferred capture compounds are marimastat (Ia) and batimastat (Ib). Another example of a small molecule moiety in a particularly preferred capture compound is sertindol (Ic), which binds to a neuro transmitter receptor:

The sorting or marker function according to any aspect or embodiment of the invention is a moiety that is capable of selectively and specifically binding to a (second) surface, or a second surface—preferably the surface of a microparticle. A particularly preferred sorting function is biotin, which binds to streptavidin with such low dissociation constant that the resulting bond is comparable to a covalent bond in dissociation energy. Biotin-streptavidin binding is an example of what is referred to here as a quasi-covalent bond.

A target cell for practicing the invention may be any non-recombinant cell having a protein or protein complex on its surface which is specifically addressable by a small molecule moiety. In one embodiment, the target cell is a cell circulating in peripheral blood. In one embodiment, the target cell is a circulating tumour cell. Not recombinantly modified mammalian cells are preferred. For the method aspects of the invention, human cells isolated from a patient and tagged ex-vivo are preferred.

According to one embodiment, a non-recombinant target cell responding to a particular pharmaceutical drug is identified, tagged and isolated. Such tagging or isolation is attained by attaching a capture compound to the cell reversibly and attaching this compound covalently in a subsequent step.

In a number of embodiments, specific sites of interaction for a small molecule moiety are not provided by one single protein on the surface of a target cell, but by structural interaction of a number of different protein molecules, which form a protein complex. It is difficult and laboursome to make and select antibodies that specifically recognize such protein complexes. Antibody based methods relying on the recognition of particular single proteins forming such complexes do not render valid diagnostic results where marking or isolating a cell depending on the presence of a specific protein complex is required. The present invention provides means for functionally addressing such complexes. The method of the invention similarly enables tagging and isolation of target cells that cannot be characterized by a specific single protein component.

The means and methods of the invention may be applied in solution. Disease-relevant cell surface protein structures can be tagged by a capture compound as described above, and subsequently identified or isolated. This can be used to achieve diagnostic objectives (detection of aberrant cells, for example) and for therapeutic objectives (removal or depletion of particular cells). The invention allows for tagging and isolation on a basis of function, thus providing advantages or complementary qualities compared to separation or identification based on recognition of particular proteins by antibodies. Two advantages are of particular importance therein relating to aspects and embodiments that make use of photoactivatable reaction functions:

Firstly, binding sites for small molecules are addressed functionally. Many binding sites for drugs and physiologically relevant messenger molecules are formed by multi protein complexes made from a plurality of single proteins that only locate together on the target cell. The individual components of such complexes usually show a distribution that is markedly different from the distribution complexes across cells and tissues. Hence, the individual protein is hardly representative of the complex in these cases.

Secondly, the protein on the target cell is bound covalently. The small molecule moiety is part of a trifunctional compound that allows for covalently binding the target by activation of the reactivity function. Further washing steps will not dissociate the bond between the cell surface and the capture compound, or the second surface attached thereto.

The reagents and methods of the invention can be employed for tagging and isolating target cells. One example is the use of the invention in methods that are analogous to immunohistochemistry, where functional small molecule binding sites can be analysed or visualized. Visualisation or analysis can be achieved by, for example, employing biotin as a sorting function on the capture compound, using streptavidin enzyme conjugates for a subsequent labelling or chemoluminescence reaction, or streptavidin-fluorescent dye conjugates for fluorescence detection. Another alternative is the use of mass tags for detection by MALDI-MS based "tissue imaging" or the use of fluorophores instead of biotin within the capture compound for direct fluorescence detection.

The reagents and methods of the invention can be employed for isolating target cells. Cells isolated from cell suspensions or body fluids may be tagged by the methods of the invention and then may be isolated, for example by fluorescence activated cell sorting (FACS). Tagged cells may also be attached to magnetic particles or solid surfaces such as chips or microtitre plates.

The following examples illustrate the practicability of the invention in its major aspects: entire cells may be tagged selectively on the basis of interacting a small molecule moiety that is part of a capture compound, with a cell surface structure on the target cell. Tagged cells are also isolated.

Figure 1:
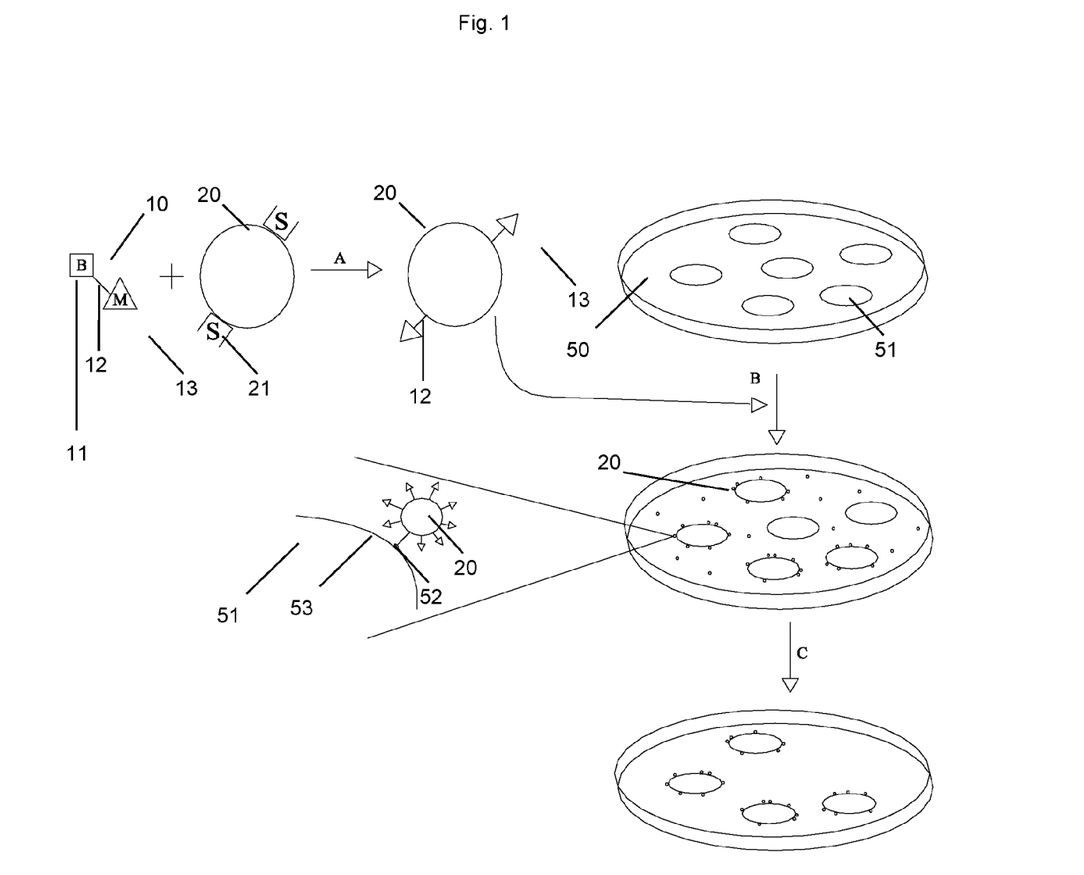
FIG. 1 shows the process of directly tagging target cells with capture compound coated particles, without photoactivation.

FIG. 1 illustrates one example of a method according to the first aspect of the invention. A capture compound 10 comprises a sorting function 11 (biotin), a selectivity function 13 (marimastat) and a central core 12. During a binding step (A) the capture compound 10 is immobilized to a magnetic particle 20 coated with streptavidin 21. During step (B) the magnetic particle 20 is added to cells 51 in a cell culture dish 50, leading to its binding on cell surface 53 of target cells 51 by MMP complexes 52. During subsequent washing step (C), surplus magnetic particles 20 are removed.

Figure 2:
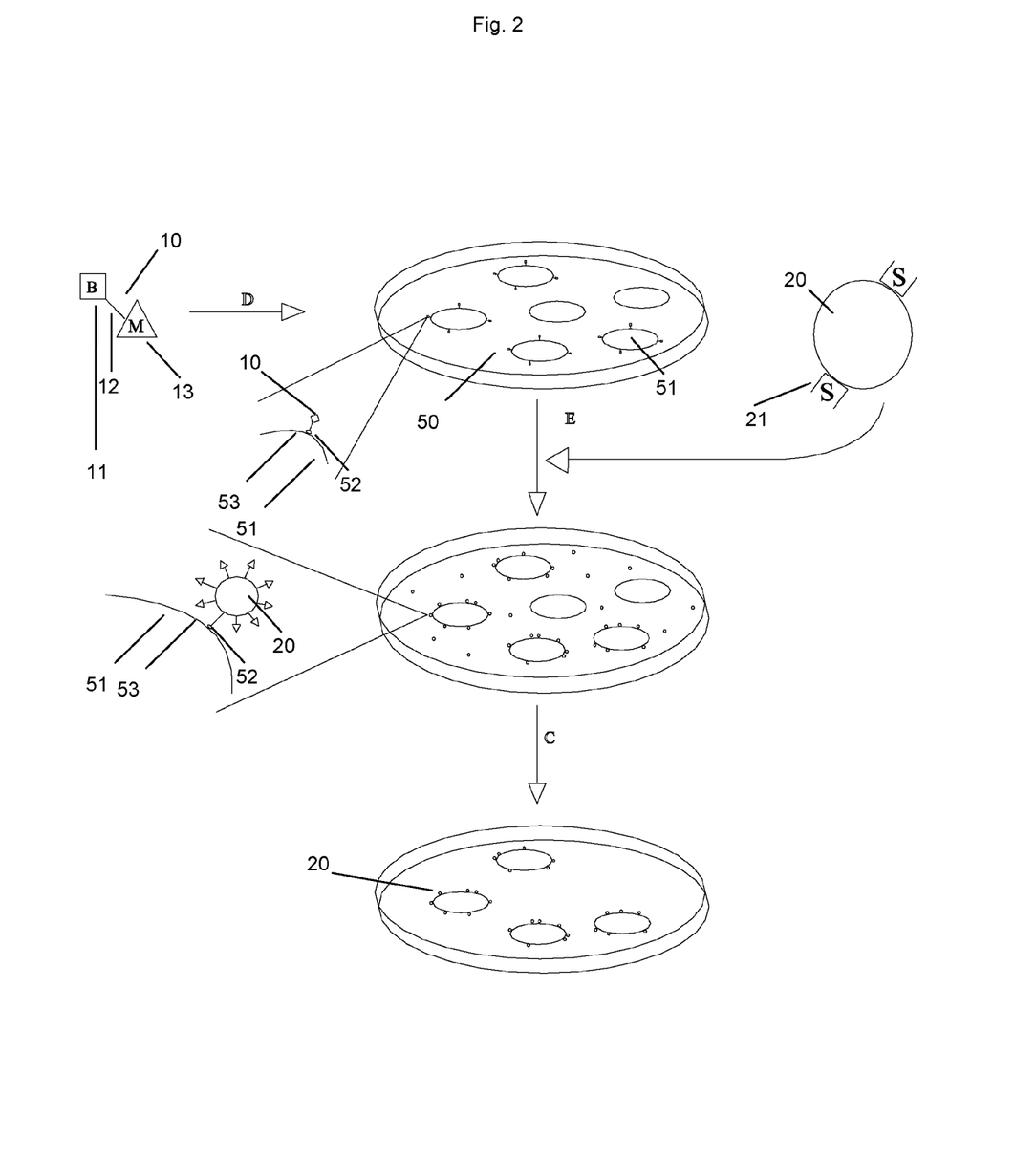
FIG. 2 shows the process of covering target cells with capture compound and subsequent attachment of tagging particles, without photoactivation.

FIG. 2 shows another example of a method according to the first aspect of the invention. Again capture compound 10 is used, comprising a sorting function 11 (biotin), a selectivity function 13 (marimastat) and a central core 12. In a first binding step (D), capture compound 10 is added to cell culture cells 51 in a cell culture dish 50. Capture compound 10 binds to the cell surface 53 of target cells 51 by MMP complexes 52 on cell surface 53. Removing of the supernatant and washing (not shown) removes excess capture compound. In a subsequent step E, streptavidin 21 coated magnetic particles 20 are added to the dish 50, leading to magnetic particles 20 to bind via biotin 11 within capture compound 12 bound to MMP complexes 52 to the cell surface 53 of target cells 51. A washing step (C) removes unattached particles.

Figure 3:
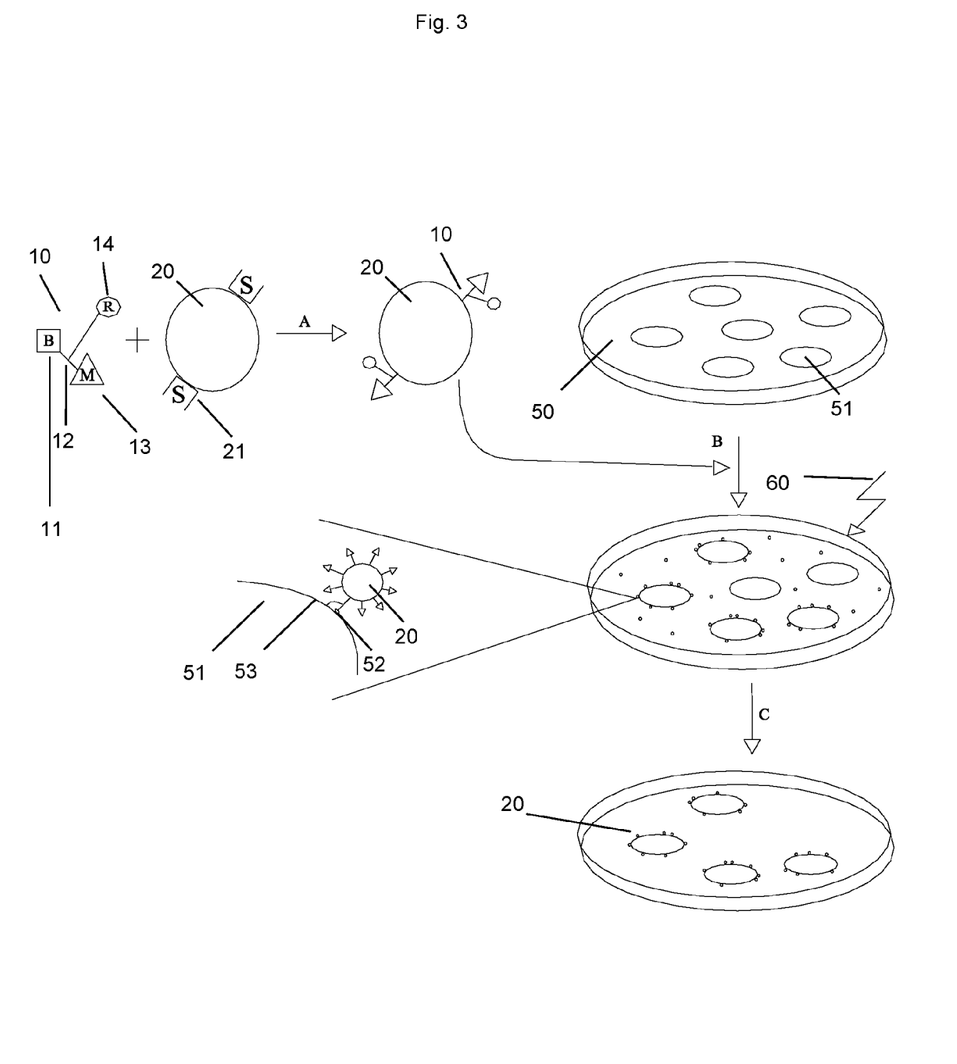
FIG. 3 shows the process of directly tagging target cells with capture compound coated particles, with photoactivation.
Figure 4:
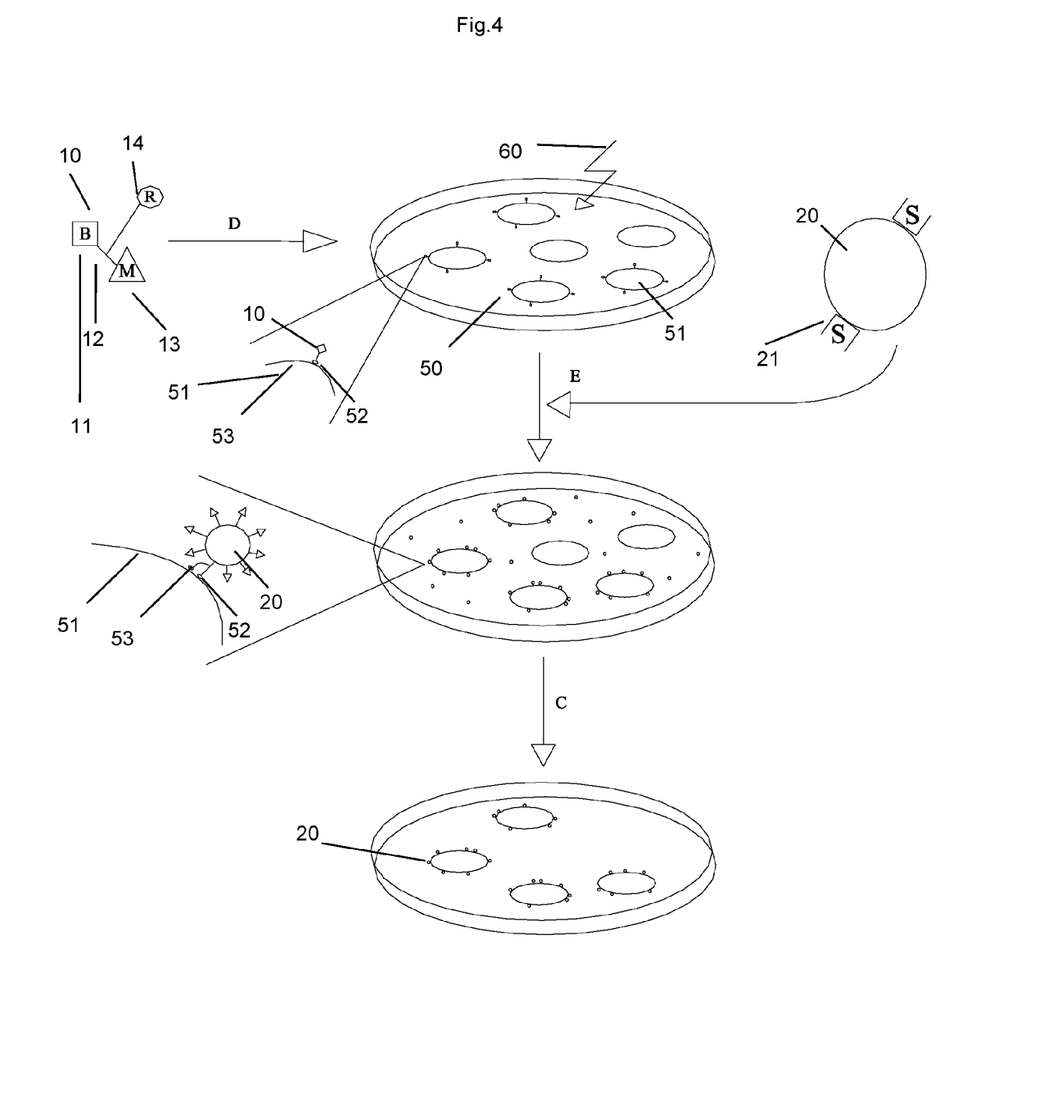
FIG. 4 shows the process of tagging target cells with capture compound and subsequent attachment of tagging particles, with photoactivation.

FIGS. 3 and 4 show analogous examples for the methods of FIGS. 1 and 2 making use of photoactivation. Capture compound 10 comprises a reactivity function 14 attached to central core 12. Magnetic particles 20 are either first coated with capture compound 10 (A in FIG. 3) and then attached to the cell surface 53 of target cells 51 by electromagnetic radiation (light). Alternatively (FIG. 4), capture compound 10 is first attached by light 60 to the cell surface 53 of target cells 51 and then contacted with magnetic particles 20.

EXAMPLES

Example 1

Synthesis of a Trifunctional Marimastat Capture Compound

The capture compound used in the following examples was synthesised as follows:

Synthesis of the compound labelled "SC" proceeded in analogy to the method described in Dalhoff et al., ChemBioChem 11, 256 ff. (2010).

Example 2a

Marimastat-Specific Tagging by Magnetic Particles

Cell culture supernatant (10% heat inactivated fetal calf serum (PAA Laboratories GmbH), 1× Penicillin/Streptomycin (PAA) in DMEM (Dulbecco's Modified Eagle Medium) High Glucose (4.5 g/l) with stable glutamin (PAA)) was removed from two cell cultures of adherent fibrosarcoma cells (cell line HT-1080 (ACC 315 Deutsche Sammlung von Mikroorganismen and Zellkulturen DSMZ Braunschweig; densely grown; 3.5 cm petri dish; passage 9) and added to further cell culture supernatant from a larger culture. The petri dish was closed to avoid drying of the cells.

20 µl 10 mg/ml strepatavidin coated magnetic particles of 1 µm diameter (Dynabeads MyOne Steptavidin C1 (Dynal)) (streptavidin magnetic particles or particles in the following) were mixed with 10 µl 100 µM marimastat capture compound V (caprotec bioanalytics GmbH)

and incubated 10 min at room temperature. The particles were collected at the inner vial wall by applying a strong magnet (caproMag, caprotec bioanalytics GmbH, containing a 150×9×7 mm neodymium magnet (NdFeB) of quality N52 (1.43 Tesla)), and the supernatant was discarded. The particles were resuspended in 500 µl HT-1080 cell culture supernatant, collected magnetically anew and resuspended in 200 µl water, giving a 1 mg/ml marimastat capture compound-particle suspension.

1 µl of this suspension was mixed with 1 µl water and 8 µl HT-1080 cell culture supernatant for adding to a HT-1080 culture labelled "ver". 1 µl of 1 mg/ml marimastat capture compound suspension was mixed with 1 µl 10 mM free marimastat (competitor) and 8 µl HT-1080 cell culture suspension for adding to a control culture "con". The concentration of the marimastat capture compound particles was thus 0.1 mg/ml.

Each 0.5 µl of these 0.1 mg/ml marimastat capture compound suspensions was added onto the cell layer of two cultures of adherent HT-1080 cells (without free marimastat in culture "ver"; with free marimastat in culture "con"). A small air bubble applied on purpose limited the running off of the suspension. Two small felt marker marks were made on the outer walls to be able to localize the areas of particle application in light microscopy. The experiments were incubated 15 min at room temperature. During this time, the sinking of the particles onto the cell layer was followed and documented by light microscopy. Particles coated with marimastat capture compound are seen as small dark spheres in the phase contrast microscope.

The corresponding cell culture container was held at an angle and the application area was washed ten times with 0.5 ml cell culture supernatant by applying pulses with the pipette to generate pressure and foam. The washing fractions were removed and a photograph was taken by light microscopy. The experiment was repeated twice. All experiments showed a similar result: After washing, cells in the culture marked "ver" were tagged on their surface by particles, cells in the culture marked "con" (control) were not marked, or to only very little extent. It is assumed that in the "control" culture, competition with an excess of free marimastat inhibits the specific binding of capture-compound coated particles, proving the selectivity of tagging.

Example 2b

Method 2 for Marimastat-Specific Cell Tagging with Magnetic Particles

Cell culture supernatant of two cell cultures of adherent fibrosarcoma cells of cell line HT-1080 was prepared as described above (example 2a).

The cultures were spiked with 400 µl cell culture supernatant each. "Ver" received 20 µl water, control "con" received 20 µl 10 mM free marimastat (competitor), both cultures were swayed for mixing and incubated 3 min at room temperature, carefully keeping the cell layer wet at all times. During this step, the free marimastat in culture "con" binds to marimastat-binding proteins or protein complexes on the surface of cells and blocks their binding sites, preventing marimastat capture compounds from binding during the subsequent step. 2 µl 100 µmol/l marimastat capture compound was added to each culture, shaken gently and incubated 5 min at room temperature. Binding of the marimastat capture compound only happens on the cell surface proteins in culture "ver" (which are not blocked). The supernatant was removed from each, both cultures were washed with 400 µl fresh cell culture supernatant twice to remove excess marimastat capture compound, and 400 µl fresh cell culture supernatant was added each. 1 µl of 10 mg/ml strepatavidin coated magnetic particles of 1 µm diameter (Dynabeads MyOne Steptavidin C1 (Dynal)), was added to each culture, homogenized by swaying and incubated 30 min at room temperature. In this example, streptavidin on the particle surface attaches to the biotin moiety of a marimastat capture compound, bound at the cell surface proteins or complexes in culture "ver". Thereby, the marimastat capture compound binds the magnetic particles to the cell surface. The supernatant was aspirated into a pipette and washed across the cell layer repeatedly to generate pressure and foam. This washing step was repeated with fresh cell culture supernatant. Magnetic particles not attached specifically to the cell surface by capture compounds are washed away. Removal of the supernatant and inspection of the cells by light microscopy gave a result analogous to the result reported for example 2a above. Culture "ver" shows particle-tagged cells, in culture "con", little or no particles are visible.

Example 3

Specific Isolation of Selectively Tagged Cells

After tagging and washing (method 2, see example 2b) the supernatant was removed from cultures "ver" and "con" and the cultures were treated with 200 µl non-enzymatic cell dissociation solution (Sigma), followed by 10 min incubation at room temperature. Repeated washing of the 200 µl solution across the cell layer resulted in complete dissociation of the cells from the cell culture container, yielding a suspension. The cells were moved to two 200 µl PCR vials labelled "ver" and "con", respectively. Cells remained intact during this procedure. A strong magnet (caproMag, caprotec bioanalytics GmbH, see example 2a) was applied to the outer wall of the vials. While cells of control "con" mostly sunk to the bottom of the vial, a significant part of the cells remained on the inner vial wall close to the magnet in sample "ver".

Example 4

Immobilization of HT-1080 Cells, SHI-1 Cells and THP-1 Cells from Suspension in the Absence and Presence of White Blood Cells HT-1080 cells (see above) were treated for 30 min in cell culture medium with calcein AM to fluorescently stain the cytosol and were provided in suspension (obtained by scraping off the adherent cells using a cell spatula) at a final concentration of ~0.5*10$^6$/ml in culture medium. White blood cells (WBC) freshly obtained from a donor by lysis of erythrocytes and subsequent washing and resuspension were adjusted to a final concentration of ~5*10$^6$/ml in phosphate buffered saline (PBS). 12-well multititer plates (streptavidin coated) were used for cell immobilization.

Samples of HT-1080 cells to be used as controls were treated with adjusted to 50 µmol/l free marimastat in medium by adding a stock solution (10 mM) of the competitor (samples marked "C"). Non-competitor verum samples are marked "A".

Samples treated with marimastat capture compound in solution were adjusted to 0.5 µmol/l capture compound in medium from 20 µmol/l stock solution (samples labelled "ind"), or attached to the capture compound-treated streptavidin-coated surface (samples labelled "dir").

For determining the influence on binding by activating the reactivity function by UV irradiation (samples labelled "UV") in samples for indirect binding (first capture compound attaching to cells, then cells binding to surface), cells were irradiated for 1 min by a near UV laboratory source ($\lambda_{max}$=310 nm, caproBox, caprotec bioanalytics GmbH, Berlin) in an uncoated well (or not for samples without UV irradiation), collected, spun down, washed, and transferred to a streptavidin-coated well (incubation time~3 h). Samples for direct binding were brought into capture compound coated wells (prepared as described below) directly (incubation time~3 h) and UV-irradiated therein (or not for samples without UV irradiation). For loading the streptavidin-coated microtiter plates with capture compound, the wells were rinsed repeatedly for 10 min with 10 µl of 20 µM marimastat capture compound per well in 200 µl PBS at room temperature; the supernatant was discarded and the wells were washed with PBS.

The medium over the cells bound to the surface was mainly removed (a minimum rest was left to cover the cells and not let the cells dry) and all wells were washed carefully two times with 1 ml medium. HT-1080 cells were counted by their calcein AM fluorescence using a Cellavista system. Values below are adjusted for HT-1080 cell numbers delivered onto the well ($1.9*10^5$).

The results for an experiment comparing binding efficiency of indirect binding in absence or presence of competitor with and without UV irradiation to activate the reactivity function are given in Table 1. All values are means of three individual samples.

TABLE 1

| Sample code | Sample | Percent input cells recovered |
|---|---|---|
| A ind UV | HT-1080, tagged by capture cmpd, UV activated | 5.6 (standard deviation of 3 experiments: 0.2) |
| C ind UV | HT-1080, marimastat excess competitor (control), UV activated | 0.7 (standard deviation of 3 experiments: 0.2) |
| A ind (no UV) | HT-1080, tagged by capture cmpd, no UV | 2.0 (standard deviation of 3 experiments: 0.3) |
| C ind (no UV) | HT-1080, marimastat excess competitor (control), no UV | 1.1 (standard deviation of 3 experiments: 0.3) |

The results given in Table 1 suggest that while capture of cells is possible marimastat-specifically without attaching the cells through a reactivity function, efficiency of capture is improved significantly by the reactivity function.

The results for an experiment comparing binding efficiency of direct binding in absence or presence of competitor with and without UV irradiation to activate the reactivity function are given in Table 2. All values are means of three individual samples.

TABLE 2

| Sample code | Sample | Percent input cells recovered |
|---|---|---|
| A dir UV | HT-1080, tagged by capture cmpd, UV activated | 60.8 (standard deviation of 3 experiments: 3.3) |
| C dir UV | HT-1080, marimastat excess competitor (control), UV activated | 7.9 (standard deviation of 3 experiments: 2.6) |
| A dir (no UV) | HT-1080, tagged by capture cmpd, no UV | 61.5 (standard deviation of 3 experiments: 3.5) |
| C dir (no UV) | HT-1080, marimastat excess competitor (control), no UV | 14.5 (standard deviation of 3 experiments: 5.0) |

The direct binding approach seems to have rendered higher binding efficiency and similar discrimination between verum and control. No significant difference between UV or no UV activation is observed.

In a separate experiment, HT-1080 cells were added in steps of tenfold multiplication to a WBC suspension and added onto the plate (direct binding mode, no UV, see above). Binding efficiencies were similar for 1:1, 1:10, 1:100 and 1:1000 dilution of HT-1080 in WBC (WBC constant 150000 cells). Similarly, binding efficiencies for HT-1080 alone were unaffected by the number of cells applied to the microwell from 150 cells to 150000 cells.

Also SHI-1 cells (Chen et al., Haematologica 2005; 90:766-775) and THP-1 cells (ATCC No TIB 202) were marimastat-specifically captured in the absence (150000 SHI-1 or THP-1) or presence of WBC (15000 SHI-1 or THP-1, constant 150000 WBC) with up to 68% and 14% efficiencies, respectively (direct binding mode, no UV, see above).

Examples 2 to 4 address human fibrosarcoma cells of line HT-1080. These cells bear multiprotein complexes comprising MMP on their surface. Such cell surface complexes are typical for metastasizing tumour cells. Circulating tumour cells (CTC) are highly relevant from a diagnostical point of view, particularly with regard to a prognosis of tumour patients. MMP are functionally important for releasing tumour cells from their original tissue and for migration to other tissues. Probably these MMP complexes on the surface of HT-1080 cells are addressed by the marimastat selectivity function of the capture compound (marimastat is a well known MMP ligand). In example 5, the exact MMP interacting with the capture compound is identified.

Example 5a

Detection of a Protein Photochemically Crosslinked by the Marimastat Capture Compound by Streptavidin-Horseradish Peroxidase Blot 5a.i) Establishing the Photochemically Induced Crosslink Between the Marimastat Capture Compound and the Target Protein on the Cell Surface and Subsequent Cell Lysis:

Five times three sterile petri dishes with 3.5 cm diameter were densely grown with adherent HT-1080 cells (passage 10, see example 2 for medium and conditions). The cell culture supernatant was collected and 400 µl of this supernatant was again applied onto the cells such that the cells were covered with a layer of cell culture supernatant. Three of the petri dishes were labeled, respectively, "A", "C", "PD", "PDC" and "noCC". To "A", "PD" and "noCC" were added 20 µl ultrapure water, respectively. To "C" and "PDC" were added 20 µl 10 mmol/l marimastat, respectively (0.5 mmol/l final concentration) and homogenized by swaying. To "A", "C", "PD" and "PDC" were added 2 µl 100 µmol/l marimastat capture compound (0.5 µmol/l final concentration) and homogenized by swaying. After a 2 min incubation, cells with supernatant of petri dishes "A", "C" and "noCC" (open lids) were irradiated for 1 min with UV light ($\lambda_{max}$=310 nm, caproBox, caprotec Bioanalytics GmbH, Berlin). Cells with supernatant of petri dishes "PD" and "PDC" were not irradiated but otherwise treated the same (incubated in caproBox for 1 min without irradiation). The supernatant was collected and discarded (in a repetition experiment, this supernatant was also analyzed as described in example 5b). The adherent HT-1080 cells were washed briefly (adding, brief swaying, removing) with 2 ml of Dulbecco's PBS (1×) (PAA The culture company, ProdNr. H21-002), respectively. The cells in the three petri dishes "A" were lysed in a total volume of 400 µl RIPA BUFFER (Sigma, ProdNr. R0278-50ML) with added 1 µl Benzonase Nuclease, recombinant (Sigma, ProdNr. E1014-250KU). The lysate was transferred into a 1.5 ml Eppendorf tube. Petri dishes "C", "PD", "PDC" and "noCC" were treated analogously. The resulting five lysates "A", "C", "PD", "PDC" and "noCC" were shock frozen in liquid nitrogen and stored at −80° C. until further processing.

5a.ii) Isolation of the Capture Compound-Protein Conjugate Using Streptavidin-Coated Magnetic Particles The lysates were thawed and centrifuged for 15 min at 21380 g and 2° C. The pellets were discarded. Samples were taken from the supernatants, supplemented with SDS sample buffer (final concentration 50 mmol/l Tris HCl, 320 mM β-mercaptoethanol, 2.5% SDS, 0.05% bromophenole blue, 10% glycerol, pH 6.8) and heated 10 min at 95° C. The samples served for later confirmation of protein input and were 2.5% of the lysates, respectively. To the remaining lysates were added 100 µl 5× wash buffer (250 mM Tris HCl, 5 mol/l NaCl, 42.5 µmol/l octyl-β-D-glucopyranoside, pH 7.5), respectively, and homogenized. Then 50 µl of well suspended streptavidin-coated magnetic particles (Dynabeads MyOne Streptavidin C1, Invitrogen Dynal, ProdNr. 350.02D) were added to the lysates, respectively, and kept in suspension for 2 h at 4° C. by constantly rotating the tubes. The particles were magnetically separated (caproMag, caprotec Bioanalytics GmbH), washed six times by re-suspending and magnetic collection with 200 µl wash buffer and once with 200 µl ultrapure water.

5a.iii) Analysis by Streptavidin-Horseradish Peroxidase Blot

25% of the washed particles were re-suspended in 7.5 µl 2×SDS sample buffer and heated for 10 min at 95° C. Separation of proteins detached from the particles was performed by SDS-PAGE side-by-side to the samples taken from the lysates (OLS ProPage 4-20% Tris/glycine pre-cast gels, OLS omniPAGE minigel electrophoresis system, SDS running buffer: 25 mM Tris base, 200 mM glycine, 0.1% SDS, pH 8.3, Running time: 90 min at constant 180 V under ice cooling of the SDS running buffer, molecular weight marker: PageRuler Plus Prestained Protein Ladder, Fermentas, ProdNo. SM1811). The transfer of the proteins onto the nitrocellulose blot membrane (Protran BA 85 nitrocellulose, 0.45 µm pore size, Whatman, ProdNo. 10401197) was performed by the wet blot procedure in transfer buffer (Pierce, ProdNo. 35040) at constant 66 V over 2 h under ice cooling of the transfer buffer. The transferred proteins were stained (MemCode Reversible Protein Stain Kit, Pierce, ProdNo. 24580) and the result was documented photographically. After destaining, the blot membrane was blocked for 30 min in 15 ml 2% skim milk (J. M. Gabler Saliter GmbH & Co. KG) in TBST buffer (50 mM Tris base, 150 mmol/l NaCl, 0.1% v/v Tween 20, pH 7.6), incubated for 15 min in 2 ml 1 µg/ml streptavidin-horseradish peroxidase (Sigma, ProdNo. S5512-1 MG) in 2% skim milk in TBST buffer and after washing (four times with 25 ml TBST buffer, once with 25 ml TBS buffer (TBST without Tween 20) in Snap i.d. from Millipore) 2 ml ECL substrate (ECL Western Blotting Substrate, Pierce, ProdNo. 32106) were evenly distributed on top of the membrane. The chemoluminescence was detected by exposing an X-ray film to the blot membrane covered with polythene foil. The molecular weight marker bands were transferred by hand onto the developed X-ray film and the result was documented photographically.

As a result, it was seen from the protein stain of the blot membrane that about the same protein amount was present in each lysate meaning that about the same cell number was used for each of the five experiments "A", "C", "PD", "PDC" and "noCC". After protein isolation using magnetic particles, the sensitivity of the protein stain on the blot membrane is not high enough to detect isolated proteins (only a band at 10-15 kDa corresponding to streptavidin monomer originating from the streptavidin-coated magnetic particles is equally observed in all experiments performed with magnetic particles).

On the X-ray film, signals corresponding to endogenously biotinylated carboxylases are observed with equal intensity in each of the corresponding samples. Additionally, one further strong signal at ~65 kDa is detected, which must be due to photochemically induced crosslinking of a protein with the marimastat capture compound (the biotin of the capture compound is detected). The signal is only present in "A" after protein isolation using magnetic particles (also weakly in "A" of the lysate samples before isolation). The signal is absent without UV irradiation ("PD" and "PDC") or without marimastat capture compound ("noCC"). Importantly, the signal is absent in the presence of an excess of marimastat as competitor. The detected signal must therefore correspond to a marimastat-binding protein.

Example 5b

Identification of the Marimastat-Binding Protein to be MMP14 by Capture Compound Mass Spectrometry (CCMS)

In a repetition of the experiment described in example 5a, the magnetic particles after the wash buffer and water wash steps (end of 5a.ii) were additionally washed six times with 200 µl 80% acetonitrile and once with 200 µl ultrapure water. The proteins captured on the particles were digested by addition of 9 µl 50 mmol/l ammonium bicarbonate and 1

µl 0.5 mg/ml trypsin (Sequencing Grade, Roche, ProdNo. 11047841001) in 1 mmol/l HCl. The particles were kept in suspension in this solution by shaking (2000 rpm) at 37° C. over night. After magnetically separating the particles, the supernatant was evaporated and the contained tryptic peptides were analyzed by nanoLC-MS/MS after dissolving them in 0.1% formic acid (equipment: Easy-nLC liquid chromatography system; Proxeon Biosystems A/S and LTQ Orbitrap Velos mass spectrometer; Thermo Scientific). The peptide and protein identification by automated sequence database search was performed on the one hand using the search algorithms SEQUEST (implemented in the Proteome Discoverer software 1.2.0.208, Thermo Scientific) and X!Tandem (The Global Proteome Machine Organization; version 2007.01.01.1, implementiert in the Scaffold software, version 3_00_03, Proteome Software Inc.) or on the other hand using MaxQuant (version 1.1.1.25, Cox, J. and Mann, M. (2008) *Nat Biotechnol* 26, 1367-72.) for label-free quantification of proteins. The human UniProtKB/Swiss-Prot database (release of January 2011 from www.expasy.org) was used for searching, which contained all thitherto known human protein sequences.

As a result, MMP14 was identified as a marimastat capture compound-interacting and marimastat-specific protein: MMP14 was only identified in the presence of the marimastat capture compound and in the absence of marimastat (competitor). MMP14 has a molecular weight of 66 kDa, which fits perfectly to the specific blot signal (~65 kDa) observed in experiment 5a. In the MaxQuant analysis, MMP14 is the highest abundant protein that is completely suppressed by marimastat (competitor). In accordance to the fact that MMP14 is a plasma membrane protein with extracellular catalytic site, MMP14 was only identified in the cellular fraction and not in analyses performed analogously using the supernatant of the cells after irradiation

REFERENCE NUMBER LIST 10) marimastat capture compound
11) biotin
12) central moiety Z
13) small molecule moiety (selectivity function)
14) reactivity function
20) magnetic particle
21) streptavidin
50) cell culture dish
51) cell culture cells
52) MMP
53) cell surface
60) light

The invention claimed is:

1. A surface for isolating a target cell, comprising the surface of a magnetic particle, the surface of a gold particle, or the surface of a fibre material, and wherein the surface is characterized by having attached to said surface covalently or quasi-covalently
   a) a small molecule moiety of below 3500 u molecular mass, which is a ligand for a matrix metalloproteinase, and
   b) a photo-activatable reactivity function.

2. The surface of claim 1, wherein said reactivity function is a diazirine, an aryl azide or a benzophenone moiety.

3. The surface of claim 1, wherein said small molecule moiety and said reactivity function are both covalently attached to a capture compound comprising an at least tri-functional central core Z.

4. A particle of between 5 nm and 20 µm in diameter having a surface according to claim 1, wherein the ligand is a MMP inhibitor moiety of the hydroxamate class.

5. The particle of claim 4, wherein the MMP inhibitor is marimastat.

6. A method for isolation of a target cell from a sample, comprising:
   contacting the surface of said target cell with a capture compound, comprising
      a small molecule pharmaceutical drug or peptide hormone of below 3500 u molecular mass, which is a ligand for a matrix metalloproteinase, and
      a sorting function, by which the capture compound can selectively be attached covalently or quasi-covalently to a second surface;
   attaching the surface of said target cell to the capture compound;
   contacting the attached target cell and capture compound with a second surface to which the capture compound can selectively be attached covalently or quasi-covalently; and
   removing the target cell, capture compound, and second surface from the sample or removing the sample from the target cell, capture compound, and second surface.

7. The method of claim 6, wherein said second surface or said capture compound further comprises a reactivity function that can be photo-activated.

8. The method of claim 7, wherein said reactivity function is a diazirine, an aryl azide or a benzophenone moiety.

9. The method of claim 6, wherein said second surface is the surface of a particle.

10. The method of claim 7, wherein said capture compound comprises an at least tri-functional central core Z, to which said small molecule moiety, said reactivity function and said sorting or tagging function are each individually attached covalently.

11. A method for isolation of a target cell from a sample, comprising contacting the surface of said target cell with a second surface; attaching the surface of said target cell to said second surface, wherein said second surface comprises the surface of claim 1; and removing said second surface from the sample, or removing said sample from said second surface.

12. The method according to claim 11, wherein said reactivity function is a diazirine, an aryl azide or a benzophenone moiety.

13. The method of claim 11, wherein said small molecule moiety and said reactivity function are both covalently attached to a capture compound comprising an at least tri-functional central core Z.

14. The method of claim 13, wherein the capture compound comprises compound V:

21 22

* * * * *